United States Patent
Kumar et al.

(10) Patent No.: US 12,053,375 B2
(45) Date of Patent: Aug. 6, 2024

(54) PROSTHETIC MITRAL VALVE WITH IMPROVED ATRIAL AND/OR ANNULAR APPOSITION AND PARAVALVULAR LEAKAGE MITIGATION

(71) Applicant: 4C Medical Technologies, Inc., Maple Grove, MN (US)

(72) Inventors: Saravana B. Kumar, Minnetonka, MN (US); Steven D. Kruse, Maple Grove, MN (US); Jeffrey R. Stone, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 50 days.

(21) Appl. No.: 17/163,910

(22) Filed: Feb. 1, 2021

(65) Prior Publication Data
US 2021/0275301 A1 Sep. 9, 2021

Related U.S. Application Data

(60) Provisional application No. 62/985,411, filed on Mar. 5, 2020.

(51) Int. Cl.
*A61F 2/24* (2006.01)

(52) U.S. Cl.
CPC .......... *A61F 2/2427* (2013.01); *A61F 2/2418* (2013.01); *A61F 2250/0048* (2013.01); *A61F 2250/0056* (2013.01)

(58) Field of Classification Search
CPC .............................. A61F 2/2418; A61F 2/2409
See application file for complete search history.

(56) References Cited

U.S. PATENT DOCUMENTS

| 4,424,833 A | 1/1984 | Spector |
| 4,503,569 A | 3/1985 | Dotter |
(Continued)

FOREIGN PATENT DOCUMENTS

| AU | 2014203064 B2 | 6/2015 |
| AU | 2015230879 A1 | 10/2015 |
(Continued)

OTHER PUBLICATIONS

International Search Report and Written Opinion issued by the US Patent Office for PCT/US2021/016127, mailed May 13, 2021.
(Continued)

*Primary Examiner* — Suba Ganesan
(74) *Attorney, Agent, or Firm* — Weiss & Arons LLP

(57) ABSTRACT

The present invention provides a prosthetic heart valve device with improved fit and/or apposition between the device frame and left atrial tissue and/or the device base and the annular tissue of the left atrium to improve shifting of the implanted device and/or mitigate paravalvular leakage. The improved fit and/or apposition arises in various embodiments by providing or allowing an asymmetrical frame and/or frame base and/or providing a lower lip to aid in conforming to the asymmetrical shape of the atrium and/or ensure firm positioning therein. An additional benefit of these arrangement(s) is mitigation of paravalvular leakage as a result of improved fit and seal. In certain embodiments, the asymmetry of the frame assists with delivery of the device into the atrium.

10 Claims, 11 Drawing Sheets

(56) References Cited

U.S. PATENT DOCUMENTS

| | | |
|---|---|---|
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,231,602 B1 | 5/2001 | Carpentier |
| 6,287,334 B1 | 9/2001 | Moll |
| 6,319,280 B1 | 11/2001 | Schoon |
| 6,319,281 B1 | 11/2001 | Patel |
| 6,332,893 B1 | 12/2001 | Mortier |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,569,196 B1 | 5/2003 | Vesely |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | Dimatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,252,682 B2 | 8/2007 | Seguin |
| 7,276,077 B2 | 10/2007 | Zadno-Azizi |
| 7,276,078 B2 | 10/2007 | Spenser |
| 7,291,168 B2 | 11/2007 | Macoviak |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,967,853 B2 | 6/2011 | Eidenschink |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| 8,029,556 B2 | 10/2011 | Rowe |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,252,051 B2 | 8/2012 | Chau |
| 8,287,538 B2 | 10/2012 | Brenzel et al. |
| 8,308,798 B2 | 11/2012 | Pintor |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,644 B2 | 4/2013 | Quadri |
| 8,414,645 B2 | 4/2013 | Dwork |
| 8,439,970 B2 | 5/2013 | Jimenez |
| 8,454,686 B2 | 6/2013 | Alkhatib |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,354 B2 | 8/2014 | Benichou |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |

(56) References Cited

U.S. PATENT DOCUMENTS

| | | | |
|---|---|---|---|
| 9,138,313 | B2 | 9/2015 | Mcguckin, Jr. |
| 9,144,493 | B2 | 9/2015 | Carr |
| 9,144,494 | B2 | 9/2015 | Murray |
| 9,155,619 | B2 | 10/2015 | Liu |
| 9,161,835 | B2 | 10/2015 | Rankin |
| 9,173,737 | B2 | 11/2015 | Hill |
| 9,192,466 | B2 | 11/2015 | Kovalsky |
| 9,226,820 | B2 | 1/2016 | Braido |
| 9,232,942 | B2 | 1/2016 | Seguin |
| 9,232,996 | B2 | 1/2016 | Sun |
| 9,248,016 | B2 | 2/2016 | Oba |
| 9,259,315 | B2 | 2/2016 | Zhou |
| 9,271,856 | B2 | 3/2016 | Duffy |
| 9,277,993 | B2 | 3/2016 | Gamarra |
| 9,289,289 | B2 | 3/2016 | Rolando |
| 9,289,292 | B2 | 3/2016 | Anderl |
| 9,295,547 | B2 | 3/2016 | Costello |
| 9,295,549 | B2 | 3/2016 | Braido |
| 9,301,836 | B2 | 4/2016 | Buchbinder |
| 9,301,839 | B2 | 4/2016 | Stante |
| 9,320,597 | B2 | 4/2016 | Savage |
| 9,320,599 | B2 | 4/2016 | Salahieh |
| 9,326,853 | B2 | 5/2016 | Olson |
| 9,326,854 | B2 | 5/2016 | Casley |
| 9,333,075 | B2 | 5/2016 | Biadillah |
| 9,345,572 | B2 | 5/2016 | Cerf |
| 9,351,831 | B2 | 5/2016 | Braido |
| 9,358,108 | B2 | 6/2016 | Bortlein |
| 9,364,325 | B2 | 6/2016 | Alon |
| 9,364,637 | B2 | 6/2016 | Rothstein |
| 9,370,422 | B2 | 6/2016 | Wang |
| 9,387,106 | B2 | 7/2016 | Stante |
| 9,402,720 | B2 | 8/2016 | Richter |
| 9,414,910 | B2 | 8/2016 | Lim |
| 9,414,917 | B2 | 8/2016 | Young |
| 9,427,316 | B2 | 8/2016 | Schweich, Jr. |
| 9,439,763 | B2 | 9/2016 | Geist |
| 9,439,795 | B2 | 9/2016 | Wang |
| 9,480,560 | B2 | 11/2016 | Quadri |
| 9,498,370 | B2 | 11/2016 | Kyle et al. |
| 9,504,569 | B2 | 11/2016 | Malewicz |
| 9,522,062 | B2 | 12/2016 | Tuval |
| 9,566,152 | B2 | 2/2017 | Schweich, Jr. |
| 9,579,194 | B2 | 2/2017 | Elizondo |
| 9,579,197 | B2 | 2/2017 | Duffy |
| 9,622,863 | B2 | 4/2017 | Karapetian |
| 9,717,592 | B2 | 8/2017 | Thapliyal |
| 9,730,791 | B2 | 8/2017 | Ratz |
| 9,737,400 | B2 | 8/2017 | Fish |
| 9,737,401 | B2 | 8/2017 | Conklin |
| 9,750,604 | B2 | 9/2017 | Naor |
| 9,763,780 | B2 | 9/2017 | Morriss |
| 9,795,477 | B2 | 10/2017 | Tran |
| 9,801,711 | B2 | 10/2017 | Gainor |
| 9,827,093 | B2 | 11/2017 | Cartledge |
| 9,839,517 | B2 | 12/2017 | Centola et al. |
| 9,839,765 | B2 | 12/2017 | Morris |
| 9,861,477 | B2 | 1/2018 | Backus |
| 9,872,765 | B2 | 1/2018 | Zeng |
| 9,877,830 | B2 | 1/2018 | Lim |
| 9,968,443 | B2 | 5/2018 | Bruchman |
| 10,004,601 | B2 | 6/2018 | Tuval |
| 10,016,274 | B2 | 7/2018 | Tabor |
| 10,016,275 | B2 | 7/2018 | Nyuli |
| 10,022,132 | B2 | 7/2018 | Wlodarski et al. |
| 10,034,750 | B2 | 7/2018 | Morriss |
| 10,039,637 | B2 | 8/2018 | Maimon |
| 10,039,642 | B2 | 8/2018 | Hillukka |
| 10,098,735 | B2 | 10/2018 | Lei |
| 10,098,763 | B2 | 10/2018 | Lei |
| 10,117,742 | B2 | 11/2018 | Braido |
| 10,143,551 | B2 | 12/2018 | Braido |
| 10,182,907 | B2 | 1/2019 | Lapeyre |
| 10,195,023 | B2 | 2/2019 | Wrobel |
| 10,226,340 | B2 | 3/2019 | Keren |
| 10,231,834 | B2 | 3/2019 | Keidar |
| 10,238,490 | B2 | 3/2019 | Gifford, III |
| 10,245,145 | B2 | 4/2019 | Mantanus |
| 10,258,464 | B2 | 4/2019 | Delaloye |
| 10,299,917 | B2 | 5/2019 | Morriss |
| 10,321,990 | B2 | 6/2019 | Braido |
| 10,327,892 | B2 | 6/2019 | O'Connor |
| 10,327,893 | B2 | 6/2019 | Maiorano |
| 10,350,065 | B2 | 7/2019 | Quadri |
| 10,357,360 | B2 | 7/2019 | Hariton |
| 10,368,982 | B2 | 8/2019 | Weber |
| 10,376,363 | B2 | 8/2019 | Quadri |
| 10,383,725 | B2 | 8/2019 | Chambers |
| 10,390,943 | B2 | 8/2019 | Hernandez |
| 10,405,974 | B2 | 9/2019 | Hayes |
| 10,433,961 | B2 | 10/2019 | Mclean |
| 10,470,880 | B2 | 11/2019 | Braido |
| 10,492,907 | B2 | 12/2019 | Duffy |
| 10,500,041 | B2 | 12/2019 | Valdez |
| 10,507,107 | B2 | 12/2019 | Nathe |
| 10,512,537 | B2 | 12/2019 | Corbett |
| 10,512,538 | B2 | 12/2019 | Alkhatib |
| 10,517,726 | B2 | 12/2019 | Chau |
| 10,524,902 | B2 | 1/2020 | Gründeman |
| 10,524,910 | B2 | 1/2020 | Hammer |
| 10,531,951 | B2 | 1/2020 | Spargias |
| 10,537,427 | B2 | 1/2020 | Zeng |
| 10,555,809 | B2 | 2/2020 | Hastings |
| 10,555,812 | B2 | 2/2020 | Duffy |
| 10,561,495 | B2 | 2/2020 | Chambers |
| 10,595,992 | B2 | 3/2020 | Chambers |
| 10,610,362 | B2 | 4/2020 | Quadri |
| 10,653,523 | B2 | 5/2020 | Chambers |
| 10,667,905 | B2 | 6/2020 | Ekvall |
| 10,667,909 | B2 | 6/2020 | Richter |
| 10,702,379 | B2 | 7/2020 | Garde |
| 10,702,380 | B2 | 7/2020 | Morriss |
| 10,709,560 | B2 | 7/2020 | Kofidis |
| 10,751,169 | B2 | 8/2020 | Chambers |
| 10,751,170 | B2 | 8/2020 | Richter |
| 10,751,172 | B2 | 8/2020 | Para |
| 10,758,265 | B2 | 9/2020 | Siegel |
| 10,758,342 | B2 | 9/2020 | Chau |
| 10,779,935 | B2 | 9/2020 | Scorsin |
| 10,779,936 | B2 | 9/2020 | Pollak |
| 10,779,968 | B2 | 9/2020 | Giasolli |
| 10,786,351 | B2 | 9/2020 | Christianson |
| 10,828,152 | B2 | 11/2020 | Chambers |
| 10,856,983 | B2 | 12/2020 | Keränen |
| 10,869,756 | B2 | 12/2020 | Al-Jilaihawi |
| 10,874,513 | B2 | 12/2020 | Chambers |
| 10,945,835 | B2 | 3/2021 | Morriss |
| 10,973,630 | B2 | 4/2021 | Torrianni |
| 10,980,636 | B2 | 4/2021 | Delaloye |
| 11,000,000 | B2 | 5/2021 | Diedering |
| 11,007,053 | B2 | 5/2021 | Braido |
| 11,007,054 | B2 | 5/2021 | Braido |
| 11,013,599 | B2 | 5/2021 | Subramanian |
| 11,026,782 | B2 | 6/2021 | Chambers |
| 11,033,275 | B2 | 6/2021 | Franano et al. |
| 11,045,202 | B2 | 6/2021 | Amplatz |
| 11,065,113 | B2 | 7/2021 | Backus |
| 11,065,116 | B2 | 7/2021 | Tegels |
| 11,065,138 | B2 | 7/2021 | Schreck |
| 11,096,781 | B2 | 8/2021 | Gurovich |
| 11,147,666 | B2 | 10/2021 | Braido |
| 11,154,239 | B2 | 10/2021 | Toth |
| 11,154,396 | B2 | 10/2021 | Dibie |
| 11,154,398 | B2 | 10/2021 | Straubinger |
| 11,197,754 | B2 | 12/2021 | Saffari |
| 11,207,176 | B2 | 12/2021 | Delaloye |
| 11,278,399 | B2 | 3/2022 | Liu |
| 11,278,406 | B2 | 3/2022 | Straubinger |
| 11,351,028 | B2 | 6/2022 | Peterson |
| 11,389,293 | B2 | 7/2022 | Torrianni |
| 11,395,734 | B2 | 7/2022 | Lee |
| 11,413,141 | B2 | 8/2022 | Morin |
| 11,419,716 | B2 | 8/2022 | Braido |
| 11,452,628 | B2 | 9/2022 | Diedering |

(56) References Cited

U.S. PATENT DOCUMENTS

| | | |
|---|---|---|
| 11,458,013 B2 | 10/2022 | Righini |
| 2001/0005787 A1 | 6/2001 | Oz |
| 2002/0072710 A1 | 6/2002 | Stewart |
| 2002/0161377 A1 | 10/2002 | Rabkin |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1 | 6/2005 | Griffin |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0016288 A1 | 1/2007 | Gurskis |
| 2007/0156233 A1* | 7/2007 | Kapadia ............... A61F 2/2418 623/2.11 |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0036479 A1* | 2/2010 | Hill .................. A61F 2/2418 623/1.26 |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197193 A1 | 8/2012 | Krolik et al. |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |

(56) References Cited

U.S. PATENT DOCUMENTS

| | | |
|---|---|---|
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramanian |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | Mcnamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0328000 A1* | 11/2015 | Ratz ............... A61F 2/2418 623/2.37 |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1* | 2/2016 | Mitra ............... A61F 2/2409 206/438 |
| 2016/0030168 A1 | 2/2016 | Spenser |
| 2016/0030169 A1 | 2/2016 | Shahriari |
| 2016/0030170 A1 | 2/2016 | Alkhatib |

(56) References Cited

U.S. PATENT DOCUMENTS

| | | |
|---|---|---|
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | Mccann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | Mckinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0242905 A1 | 8/2016 | Chambers |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0042721 A1* | 2/2018 | Chambers ............... A61F 2/24 |
| 2018/0055629 A1 | 3/2018 | Oba et al. |
| 2018/0092744 A1 | 4/2018 | Von Oepen |
| 2018/0116843 A1 | 5/2018 | Schreck |
| 2018/0116848 A1 | 5/2018 | Mchugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | Peterson et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0216597 A1 | 7/2019 | Chambers |
| 2019/0224028 A1 | 7/2019 | Finn |
| 2019/0247189 A1 | 8/2019 | Dale |
| 2019/0247190 A1 | 8/2019 | Nathe |
| 2019/0247191 A1 | 8/2019 | Chambers et al. |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1 | 12/2019 | Chambers |
| 2020/0000592 A1 | 1/2020 | Lee |
| 2020/0030088 A1 | 1/2020 | Vidlund |
| 2020/0030507 A1 | 1/2020 | Higgins |
| 2020/0069423 A1 | 3/2020 | Peterson |
| 2020/0069449 A1 | 3/2020 | Diedering |
| 2020/0100897 A1 | 4/2020 | Mclean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |

(56) References Cited

U.S. PATENT DOCUMENTS

| | | |
|---|---|---|
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson |
| 2021/0236276 A1 | 8/2021 | Diedering |
| 2021/0275297 A1 | 9/2021 | Berndt |
| 2021/0290383 A1 | 9/2021 | Chambers |
| 2022/0031451 A1 | 2/2022 | Spence |
| 2022/0338979 A1* | 10/2022 | Benichou .............. A61F 2/2409 |
| 2023/0218397 A1 | 7/2023 | Chambers et al. |
| 2023/0372089 A1 | 11/2023 | Kumar |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 102036622 | 4/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 108348270 | 7/2018 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | 1996/30060 | 10/1996 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |
| WO | WO2019006387 | 1/2019 |

OTHER PUBLICATIONS

International Search Report and Written Opinion in Application No. PCT/US2021/016127, May 13, 2021.

Reed Miller, Start-Up Spotlight: 4C Addresses Mitral Regurgitation with Unique 'Dome' Device, https://medtech.citeline.com/MT105076/StartUp-Spotlight-4C-Addresses-Mitral-Regurgitation-With-Unique-Dome-Device Published by Citeline on Jun. 29, 2017.

A Novel Transcatheter Mitral Valve Replacement System, Dr. Phillippe Genereux, MD, Jun. 14, 2017.

The AltaValve™. Attributes, Challenges, and Future Programs, Dr. Philippe Genereux, MD, Jun. 22, 2018.

4C Medical's AltaValve: The First-in-Human Experience, Josep Rodes-Cabau, MD, Sep. 21, 2018.

Ferreira-Neto et al., "Transcatheter Mitral Valve Replacement With a New Supra-Annular Valve-First-in-Human Experience with the AltaValve System," https://doi.org/10.1016/j.jcin.2018.10.056, By the American College of Cardiology Foundation Published by Elsevier, Jan. 28, 2019.

Goel et al., "Transcatheter Mitral Valve Therapy with Novel Supra-Annular AltaValve," https://doi.org/10.1016/j.jaccas.2019.10.034, Published by Elsevier on behalf of the American College of Cardiology Foundation, Dec. 18, 2019.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

Extended European Search Report in Application No. 21763570.5, Mar. 22, 2024.

* cited by examiner

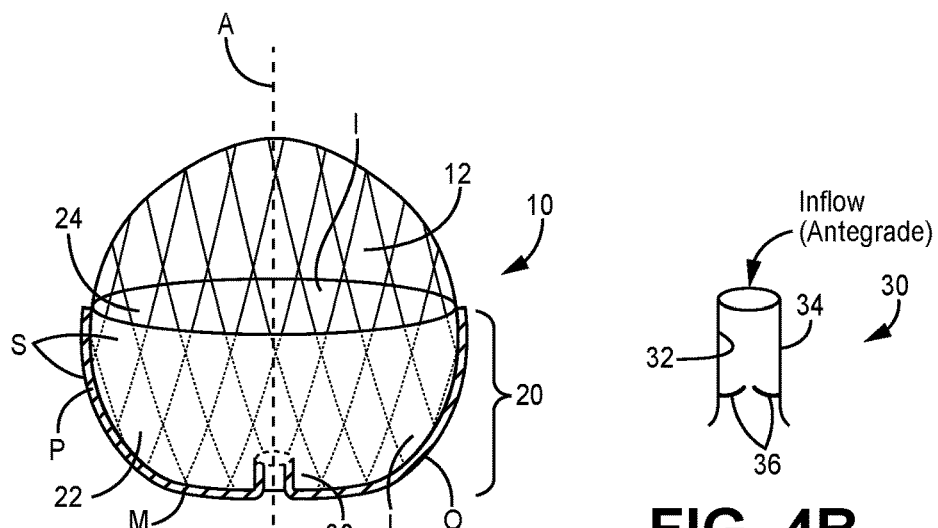
FIG. 4A
FIG. 4B
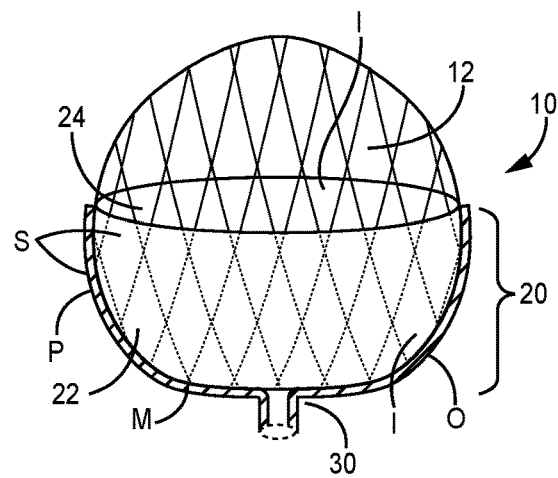
FIG. 5
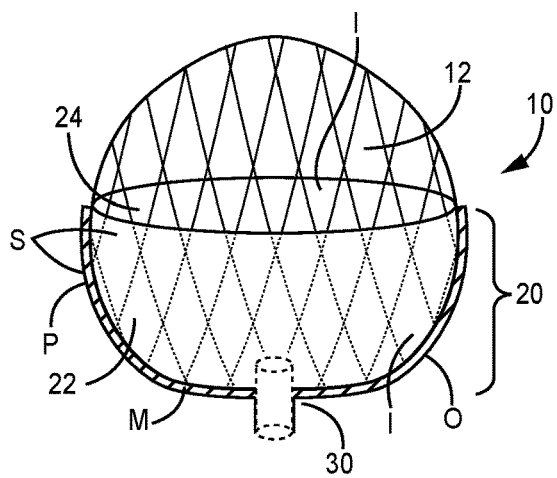
FIG. 6

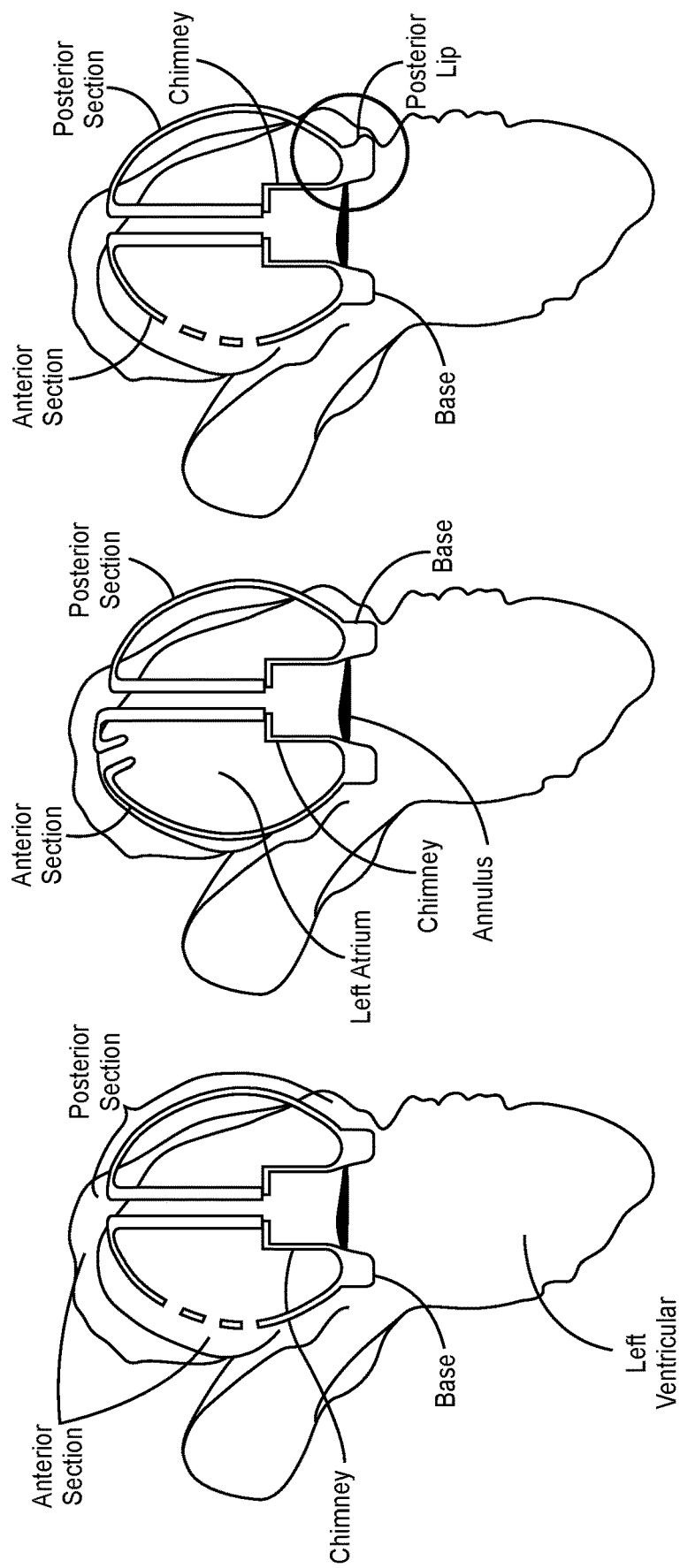

PROSTHETIC MITRAL VALVE WITH IMPROVED ATRIAL AND/OR ANNULAR APPOSITION AND PARAVALVULAR LEAKAGE MITIGATION

CROSS-REFERENCE TO RELATED APPLICATIONS

This application claims priority to provisional application No. 62/985,411, filed Mar. 5, 2020 and titled PROSTHETIC MITRAL VALVE WITH IMPROVED ATRIAL AND/OR ANNULAR APPOSITION AND PARAVALVULAR LEAKAGE MITIGATION, the contents of which are incorporated hereto in its entirety.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber. More specifically, the invention relates to improved apposition of the implanted prosthetic heart valve with the left atrium and/or the annulus as well as improving paravalvular leakage and improved delivery and/or recapture.

Description of the Related Art

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

FIG. 2 illustrates the relationship between the left atrium, annulus, chordae tendineae and the left ventricle relative to the mitral valve leaflets. As is shown, the upper surface of the annulus forms at least a portion of the floor or lower surface of the left atrial chamber, so that for purposes of description herein, the upper surface of the annulus is defined as marking the lower boundary of the left atrial chamber.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure. FIG. 3 illustrates regurgitant blood flow with an exemplary dysfunctional mitral valve.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus as designated by line or plane A, instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Transseptal delivery involves creating an access hole in the septum between the right and left atria. Once the delivery and implantation of the prosthetic heart valve device is achieved, the septal hole either remains open to heal on its own, or is sealed at least partially. Transseptal delivery, as well as the other delivery techniques, may require recapture of an at least partially deployed or expanded device within the distal lumen of the delivery catheter in order to reposition and/or reorient the device before delivering, expanding, positioning and implanting the device.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, all known prosthetic heart valves are intended for full replacement of the native heart valve. Therefore, these replacement heart valves, and/or anchoring or tethering structures, physically extend out of the left atrial chamber, in the case of mitral valves, and engage the inner annulus and/or valve leaflets, in many cases pinning the native leaflets against the walls of the inner annulus, thereby permanently eliminating all remaining functionality of the native valve and making the patient completely reliant on the replacement valve. In other cases, the anchoring structures extend into the left ventricle and may anchor into the left ventricle wall tissue and/or the sub-annular surface at the top of the left ventricle. Others may comprise a presence in, or engagement with, a pulmonary artery.

Obviously, there will be cases when native valve has lost virtually complete functionality before the interventional implantation procedure. In this case the preferred solution will comprise an implant that does not extent outside of, e.g., the left atrium, and that functions to completely replace the native valve function. However, in many other cases, the native valve remains functional to an extent and may, or may not, continue to lose functionality after the implantation procedure. A preferred solution in this case comprises delivery and implantation of a valve device that will function both as a supplemental or augmentation valve without damaging the native leaflets in order to retain native valve leaflet functionality as long as present, while also being fully capable of replacing the native function of a valve that slowly loses most or all of its functionality post-implantation of the prosthetic valve.

In all cases, including two-chamber solutions, paravalvular leakage (PVL) may develop as a result of insufficient sealing or apposition of the prosthetic valve device and the native chamber tissue, including but not limited to annular sealing which, in some cases, may result from movement of the implanted device within the heart chamber. In the case of the exemplary mitral valve, PVL results in a retrograde leak of blood from the left ventricle to the left atrium, reducing the efficiency of the heart. Lack of sealing apposition may occur for several reasons.

For example, patients may have at least some calcification in the heart chamber, particularly in the annular surface which works to reduce compliance of that calcified tissue. This reduced compliance reduces the ability of the tissue and the prosthetic heart valve device to seal together on implantation, leaving gaps between tissue and device. The mitral valve annulus and the tricuspid valve annulus may be affected by calcification, leading to poor sealing apposition with the implanted prosthetic heart valve device and PVL.

As shown in the Figures, the left atrium further comprises an asymmetric shape which can result in suboptimal apposition by the device's frame against the atrial walls and/or tissue and/or the device's base against the annulus.

Certain inventive embodiments described herein are readily applicable to single or two chamber solutions, unless otherwise indicated. Moreover, certain embodiments discussed herein may be applied to preservation and/or replacement of native valve functionality generally, with improved apposition and/or PVL mitigation and/or delivery/recapture, and are not, therefore, limited to the mitral valve and may be extended to include devices and methods for treating the tricuspid valve, the aortic valve and/or pulmonary valves.

Various embodiments of the several inventions disclosed herein address these, inter alia, issues.

BRIEF SUMMARY OF THE INVENTION

The present invention provides a prosthetic heart valve device with improved fit and/or apposition between the device frame and left atrial tissue and/or the device base and the annular tissue of the left atrium to improve shifting of the implanted device and/or mitigate paravalvular leakage. The improved fit and/or apposition arises in various embodiments by providing or allowing an asymmetrical frame and/or frame base and/or providing a lower lip to aid in conforming to the asymmetrical shape of the atrium and/or ensure firm positioning therein. An additional benefit of these arrangement(s) is mitigation of paravalvular leakage as a result of improved fit and seal. In certain embodiments, the asymmetry of the frame assists with delivery of the device into the atrium.

BRIEF DESCRIPTION OF THE SEVERAL VIEWS OF THE DRAWINGS

FIG. 4A illustrates a partial cutaway side view of one embodiment of the present invention.

FIG. 4B illustrates a side cutaway view of one embodiment of a valve support.

FIG. 5 illustrates a partial cutaway side view of one embodiment of the present invention.

FIG. 6 illustrates a partial cutaway side view of one embodiment of the present invention.

FIG. 18A illustrates a cutaway view of one embodiment of a mandrel of the present invention.

FIG. 19A illustrates a cutaway view of one embodiment of a mandrel of the present invention.

FIG. 20A illustrates a cutaway view of one embodiment of a mandrel of the present invention.

DETAILED DESCRIPTION OF THE INVENTION

Figure 1:
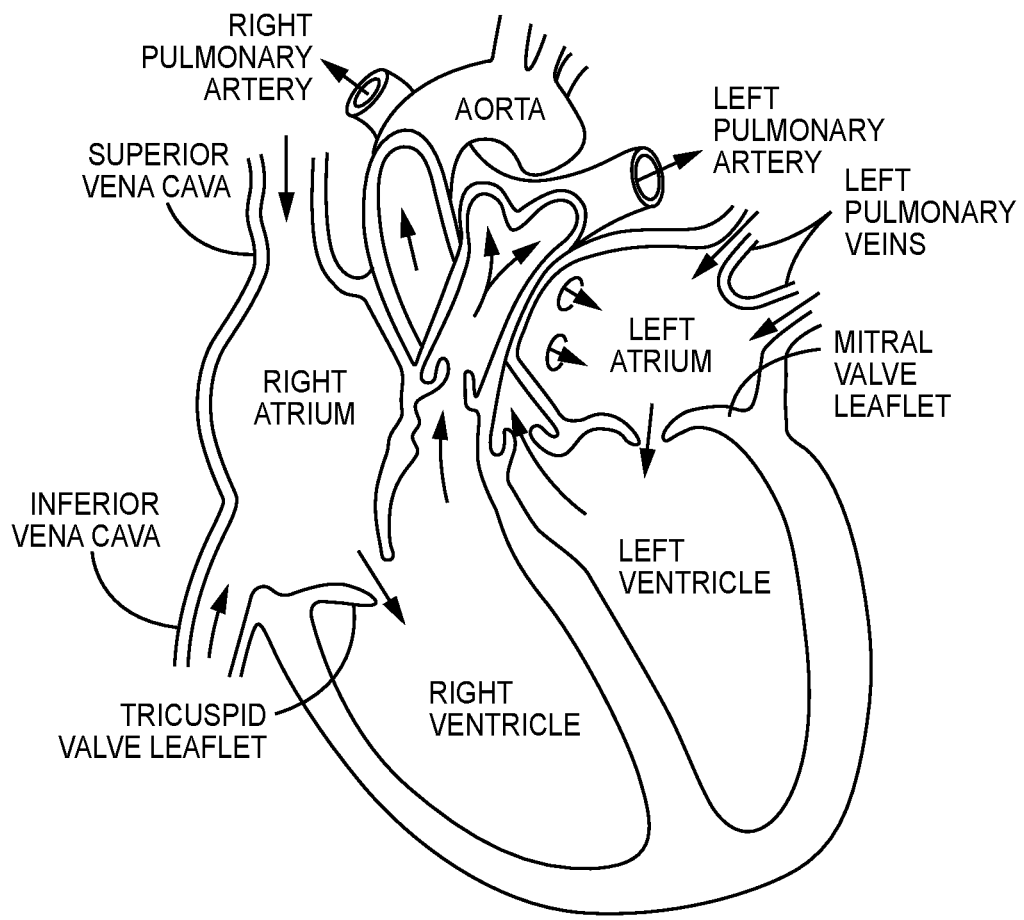
FIG. 1 illustrates certain features of the heart in cross-section.
Figure 2:
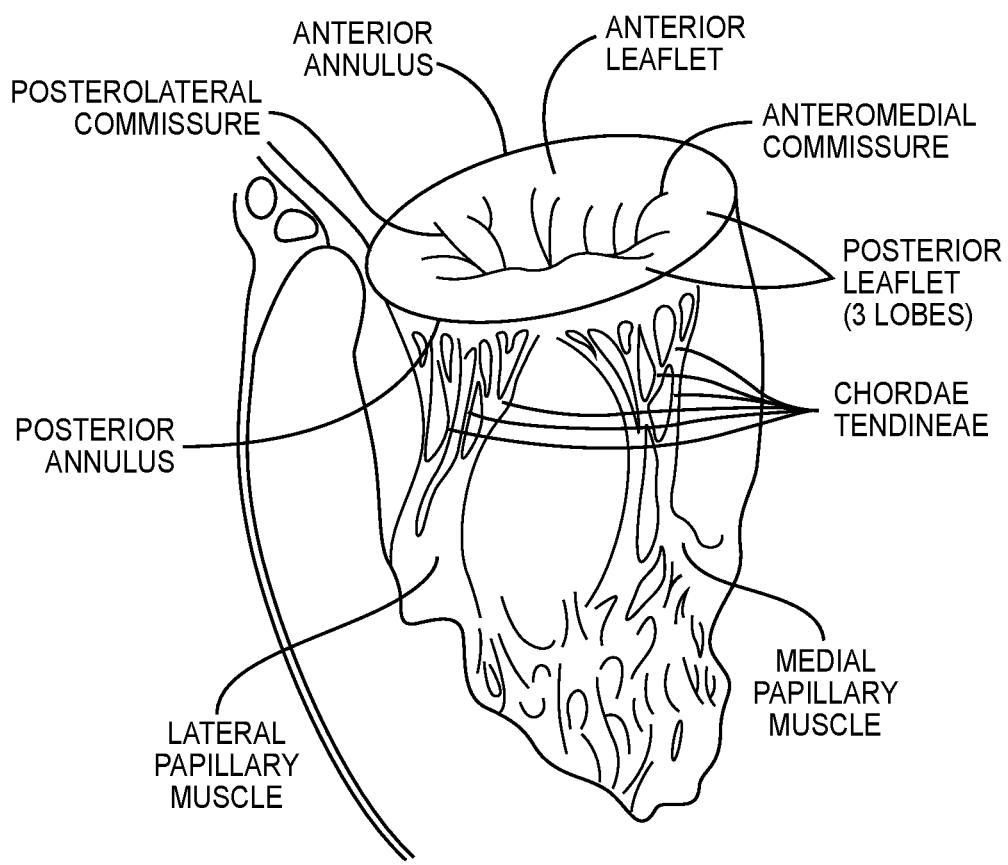
FIG. 2 illustrates a cross-sectional perspective view of the left side of the heart.
Figure 3:
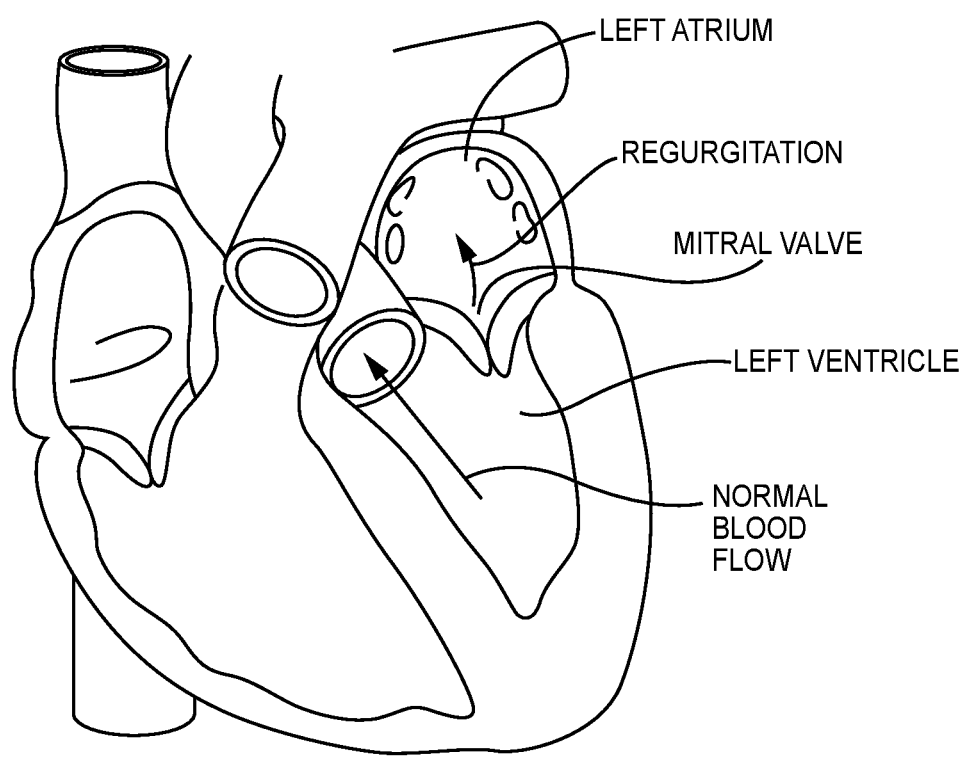
FIG. 3 illustrates a cross-sectional view of the heart showing retrograde blood flow resulting from mitral valve regurgitation compared with normal blood flow.

Various embodiments of the present invention comprise a prosthetic heart valve anchoring solution that combines improved PVL mitigation through improved sealing and/or apposition between the implanted device and the heart chamber tissue.

The invention will be described in the context of an exemplary single-chamber expanded and implanted device structure comprises certain exemplary embodiments as shown in FIGS. 4A-11B and 16-17. As stated above, however, the various embodiments of the invention extend to implanted prosthetic heart valve devices generally including but not limited to 1 and/or 2-chamber solutions. Moreover, various embodiments of the invention are described as relating to prosthetic mitral valve devices. However, it will be readily appreciated by the skilled artisan that these embodiments may be applied to supplement and/or replace the functionality of heart valves generally.

With specific reference to FIGS. 4A-6, exemplary embodiments of a collapsible, and expandable, anchoring structure 10 comprising an expandable stent frame 12, or other expandable material such as a wire mesh and/or a shape memory metal or polymer or the equivalent comprising an expandable and collapsible web or interconnected cells as is known in the art. Anchoring structure 10 preferably may be biased to expand to achieve the expanded state from a collapsed state, though other collapsed-to-expanded mechanisms may also be employed. Further, anchoring structure 10 may comprise a base section 20 that may be formed of the expandable stent frame 12 or equivalent and, therefore may achieve a plurality of expanded states in order to expand and contract with the natural movements of the heart chamber walls and the annulus, including the upper annular surface and/or portions of the inner throat of the annulus located between the upper annular surface or floor of the exemplary left atrium and the left ventricle.

Base section 20 comprises an outer surface 22 and an inner surface 24 and comprises a valve support 30 either integrally formed from the base section or operatively engaged or otherwise attached to base section. Valve support 30 comprises an inner surface 32 and an outer surface 34 wherein valve support 30 is adapted to substantially align with the subject annulus and allow one-way, antegrade blood flow therethrough while preventing retrograde blood flow as a result of prosthetic leaflet(s) 36 disposed on the inner surface 32 of valve support 30.

Figure 8:
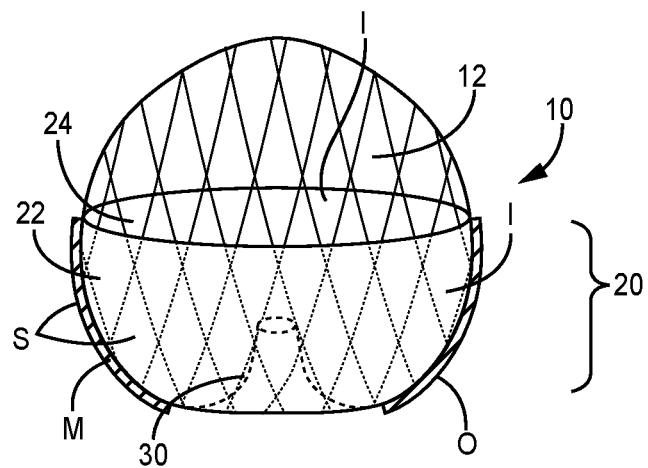
FIG. 8 illustrates a partial cutaway side view of one embodiment of the present invention.
Figure 9:
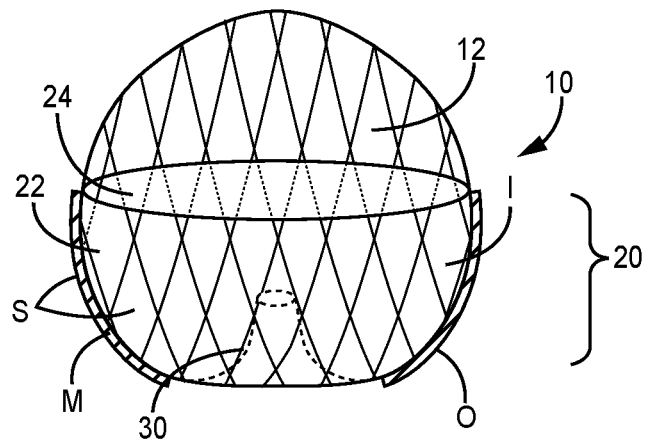
FIG. 9 illustrates a partial cutaway side view of one embodiment of the present invention.
Figure 10:
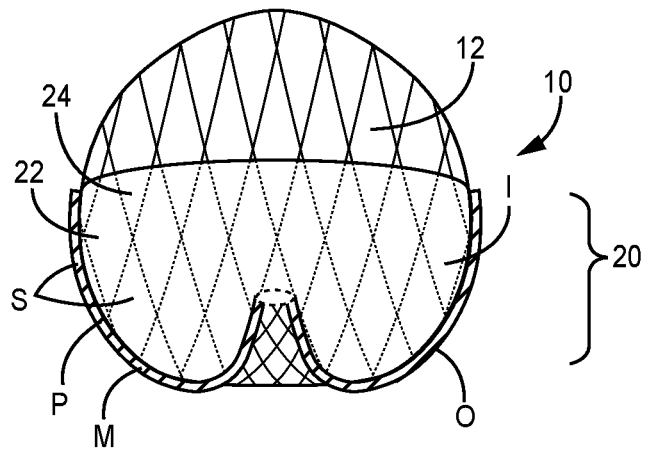
FIG. 10 illustrates a partial cutaway side view of one embodiment of the present invention.
Figure 11A:
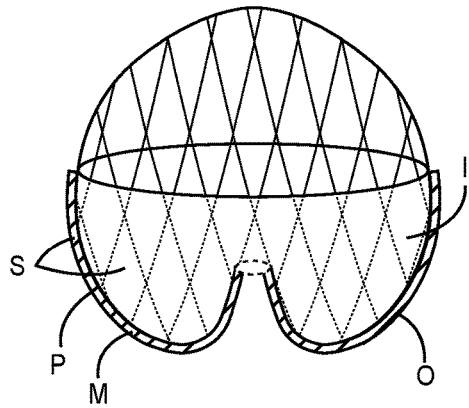
FIG. 11A illustrates a partial cutaway side view of one embodiment of the present invention.
Figure 11B:
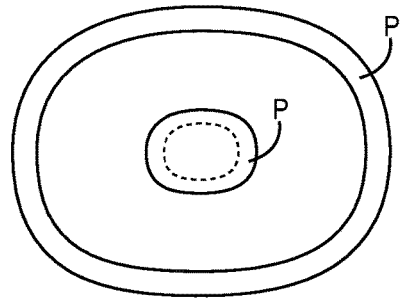
FIG. 11B illustrates a top cutaway view of one embodiment of the present invention.
Figure 12:
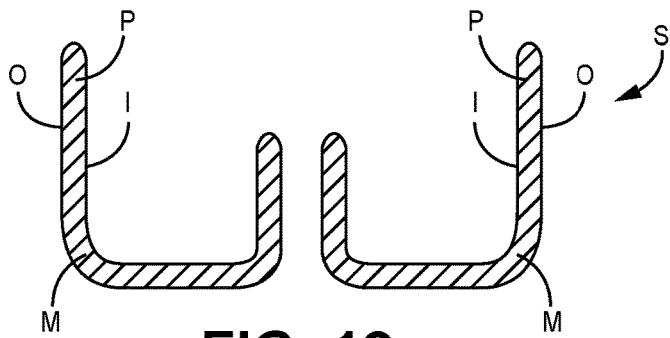
FIG. 12 illustrates a side cutaway view of one embodiment of the present invention.

Valve support 30 may be disposed wholly or at least partially within base section 20 or may, in alternate embodiments, completely extend away from base section 20 with no part of valve support 30 within the base section 20. Thus, as shown in FIG. 4A, valve support 30 is disposed entirely within base section 20. FIG. 5 illustrates the valve support 30 extending generally entirely outside base section 20. FIG. 6 illustrates the valve support 30 partially within base section 20 and also extending away from, and outside of, base section 20. FIG. 8 illustrates a variation of the valve support 30 of FIG. 4A in that the valve support 30 is formed integrally with base section 20.

Figure 7:
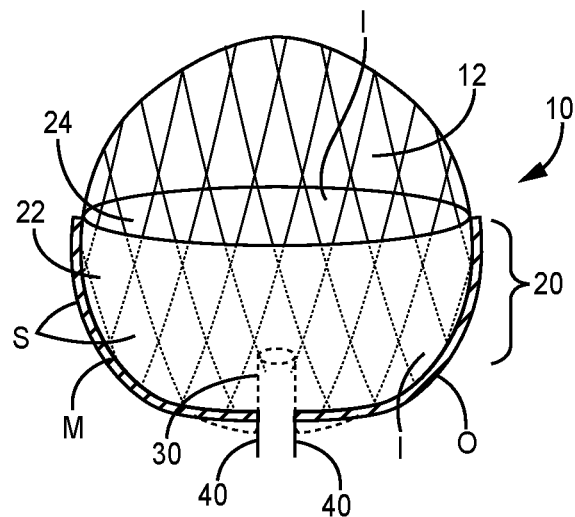
FIG. 7 illustrates a partial cutaway side view of one embodiment of the present invention.

Reference is now made to exemplary boss structure 40 shown in FIG. 7, which when present may be used to align the anchoring structure 10 in the annulus and, in combination with the base section 20, assist with sealing apposition against portions of the annulus including the annular surface and inner throat of the annulus within which boss 40 extends. Boss 40 may be used in combination with any of the structures described herein including, as shown attached to or integrally formed from base section 20 and aligned with, and/or effectively extending, the flow channel defined within valve support 30. In this sense, boss 40 is similar to the extended valve support 30 of FIG. 6, but the boss 40 does not support prosthetic leaflets therein. In other embodiments, portions of the anchoring structure, including the valve support 30 and/or boss 40, may extend downstream in the antegrade direction away from the upper surface of the annulus into the inner throat of the annulus. In some cases, the structure may extend downward to pin the native leaflets. In other cases, the structure may extend downward into the annulus but stopping short of pinning the native leaflets.

Other variations of prosthetic valve devices are known in the art and will also benefit from variations of the present invention.

It is known to cover at least a portion, typically the lower outer portion, of an anchoring frame for a prosthetic heart valve with some fabric or tissue to help prevent PVL. Known embodiments create bunching and the like of the covering material to form a seal against PVL. These solutions however do not properly solve the fit and/or apposition problems arising from annular calcification and/or the varying and variety of the annular landscape.

Thus, with reference to the Figures, base section's outer surface 22 may be at least partially covered with a skirt S formed from, or comprising, a material M that conforms and seals with portions of the atrial wall and/or the upper annular surface. In some embodiments as illustrated, portions of the anchoring structure 10 and/or the valve support 30 may extend a distance into the annular throat, i.e., below the annular surface toward the native leaflets, wherein at least some of the anchoring structure 10 and/or valve support 30 may be covered with material M.

In some embodiment, the material M may seal with at least part of the circumferential region of the wall that encompasses the left atrial appendage (LAA) within the exemplary left atrium in order to seal the LAA.

Material M may comprise a substance or compound that is hydrophilic, wherein a skirt for base section 20 may be formed, in whole or in part, from at least material M and also be hydrophilic. In this case, the hydrophilic skirt may absorb water from the patient's blood and expand or swell to provide a tightened seal and/or apposition between the base section 20 and relevant regions of the heart chamber, thereby serving as a barrier to retrograde blood flow upon implantation, mitigating and/or preventing PVL.

The hydrophilic material M may comprise a hydrophilic gel and/or hydrophilic polymer, for example that can be selected with a swelling modulus, or more than one swelling modulus, to help ensure that the swollen material M and/or hydrophilic skirt comprising material M swells to the "right" size and further ensure that the swelling process occurs slowly and gently to allow for the device to be properly positioned in the heart chamber before substantial swelling occurs. An exemplary hydrophilic hydrogel may comprise poly(vinyl alcohol) (PVA).

The hydrogel embodiment of material M may comprise hydrophilic polymer(s) that have been chemically, physically and/or ionically crosslinked to form a matrix that swells in water. The degree of swelling of hydrogels in water is determined by a balance between the free energy of polymer/solvent mixing, ionic interactions and elastic forces and is influenced by the extent of crosslinking and the chemical nature of the polymer. The degree of swelling, in turn, determines the mesh size of the hydrogel. Hydrophilic hydrogels and/or polymers may be temperature responsive and/or pH-responsive. Some, such as chitosan and alginate are naturally occurring and offer both natural hydrophilicity and biocompatibility. Still further, swelling may be initiated by mechanical means such as agitation.

Other hydrophilic materials such as hydrophilic metals may comprise portions of the anchoring structure 10.

The hydrophilic material M may be encapsulated within easily breakable, or dissolvable or biodegradable or bioerodable nanoparticles, wherein when the nanoparticles are broken, the hydrophilic material M is exposed to water and begin the swelling process. In this case, the prosthetic heart valve device will be positioned and implanted before any substantial swelling can occur.

Figure 13:
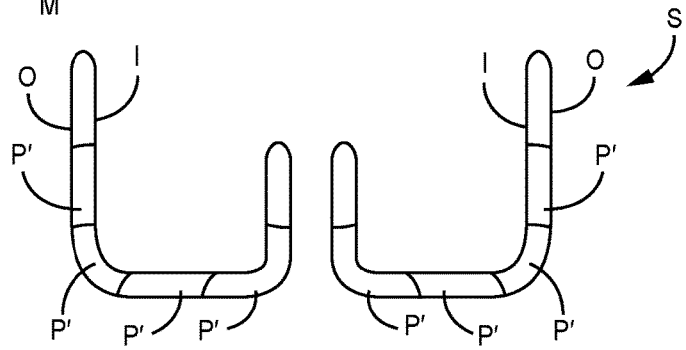
FIG. 13 illustrates a side cutaway view of one embodiment of the present invention.
Figure 14:
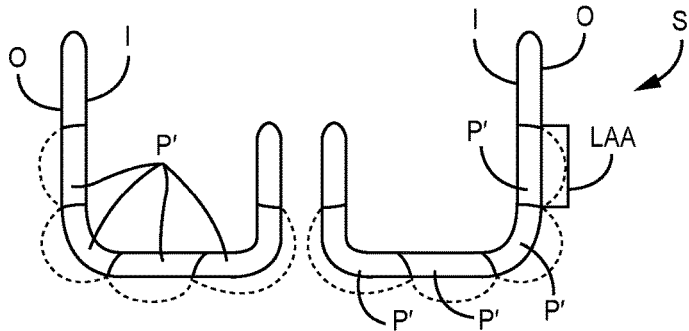
FIG. 14 illustrates a side cutaway view of one embodiment of the present invention.
Figure 15:
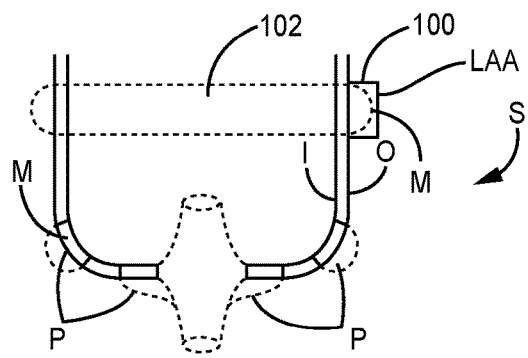
FIG. 15 illustrates a side cutaway view of one embodiment of the present invention.

Skirt S may comprise two layers of material, an inner layer I attached to the outer surface 22 of base section 20, and an outer layer O wherein the inner and outer layer form a pocket or a series of pockets P. The hydrophilic material M may be disposed or attached or incorporated at designed areas within the pocket or series of pockets to facilitate swelling at the interfacing regions between the expanded device and the patient's anatomy that are most vulnerable to PVL. For example, pocket or pockets may be arranged around the bottom surface of base section 20 and/or at least partially upward therefrom. Exemplary skirts S comprising pocket(s) P are shown in the Figures, with particular reference to FIGS. 12-15. As shown in FIGS. 13-15, subpockets P' may be provided within the two-layered skirt to provide discrete locating of the hydrophilic material M at regions particularly susceptible or vulnerable to insufficient apposition and/or PVL. As shown in FIG. 14, at least some subpockets P' may be formed and configured to swell radially outwardly to, inter alia, seal and in some cases partially fill the left atrial appendage or LAA.

In embodiments as in FIGS. 5-7 and 15-17, wherein the valve support 30, or boss 40 or other structure, extends at least partially outwardly from base section 20, the skirt S may cover at least part of the outer surface 34 of the valve support 30, with hydrophilic material M integrated or otherwise comprising the skirt S including but not limited to inclusion in pocket(s) P and/or subpockets P' formed as described above.

In the embodiment comprising a boss structure, or other extension into the inner throat of the annulus, pocket(s) P and/or subpockets P' comprising material M may be formed between the boss structure and the base section 20 to swellingly close any gap between the device and the patient's anatomy. This is best shown in FIG. 15.

Alternatively, in the embodiments comprising encapsulated hydrophilic material M, the nanoparticles or capsules may be integrated, or incorporated into, or coated, attached or adhered to, the skirt in at least the PVL-vulnerable areas discussed above. Still more alternatively, the nanoparticles or capsules carrying hydrophilic material M may be affixed or adhered or coated onto or integrated into the skirt.

Figure 16:
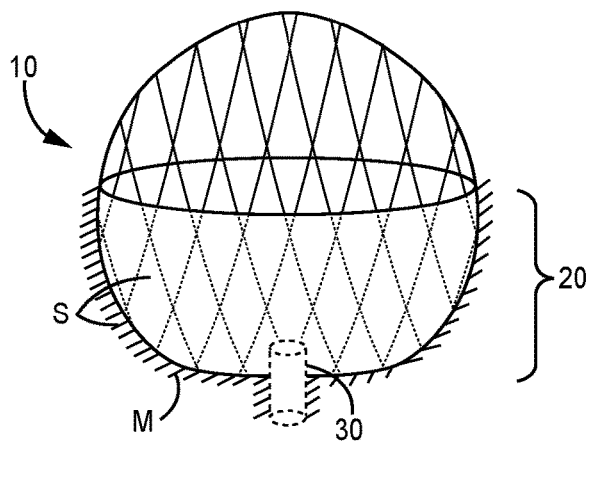
FIG. 16 illustrates a side view of one embodiment of the present invention.
Figure 17:
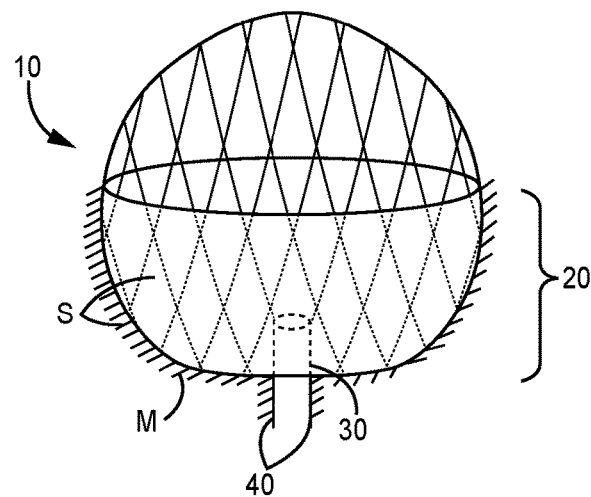
FIG. 17 illustrates a side view of one embodiment of the present invention.

In certain embodiments, therefore, a pocket P formed in skirt S is not required and the skirt S may be formed of, or comprise, a single layer of material, with the hydrophilic material M affixed or adhered or coated thereon, or integrated therein, in either encapsulated or non-encapsulated forms. FIGS. 16 and 17 illustrate exemplary single layer skirts S comprising hydrophilic material M.

In alternative embodiments, portions of the anchoring structure 10 may be at least partially formed from hydrophilic material M and may be covered or overcoated by a thin film of biodegradable, dissolvable, bioerodable and/or bioabsorbable material to delay solute interaction, and resulting swelling, with hydrophilic material M. For example, and without limitation, boss structure 40, or other extension into the inner throat of the annulus, may comprise a hydrophilic polymer that swells when contacted with a solute, e.g., water within blood. In this embodiment, a biodegradable, bioerodable and/bioabsorbable thin coating layer may be applied over the boss structure 40 to appropriately delay swelling until after implantation is achieved. The outer portions of the boss structure 40, i.e., those portions that are juxtaposed by and/or within the annulus and/or inner throat of the annulus, may comprise the hydrophilic material, e.g., polymer, so that only the outer portion of boss structure 40 swells in response to solute contact, leaving the dimensions of the inner boss structure 40 unaltered. Other areas of the anchoring structure 10 may also be formed from hydrophilic material M, e.g., a polymer(s), e.g., key struts or cells of the anchor 10 may comprise hydrophilic polymer that swells on solute contact.

Further, portions of anchoring structure 10 may also comprise a skirt S comprising a thin film of hydrophilic material M that may also be covered, or overcoated, temporarily during delivery and implantation by a biodegradable, dissolvable, bioerodable and/or bioabsorbable thin film layer as described above.

Moreover, nanoparticles encapsulating hydrophilic material M as described above may be adhered or coated onto portions of anchoring structure 10 to comprise skirt S. These nanoparticles may be overcoated with a thin biodegradable, dissolvable, bioerodable and/or bioabsorbable thin film to ensure adherence to the anchoring structure during delivery and implantation.

Each of the possible embodiments described above for implementing hydrophilic skirt comprising or incorporating hydrophilic material M may be used to cover portions of various configurations of prosthetic heart valve devices. Exemplary embodiments wherein the valve support 30 is formed from, or otherwise integrated or attached with, base section 20 are shown in FIGS. 4A, 8-10, 11A and 16-17. In this case, hydrophilic skirt S comprising hydrophilic material M as discussed above may cover the outer surface 22 of base section 20, extending to cover the bottom of base section 20 and extending further upward within base section 20 to cover the inner surface 32 of valve support 30.

In some embodiments, sealing of the left atrial appendage (LAA) may be an objective. In these cases, as shown in FIG. 15, a hydrophilic skirt S comprising hydrophilic material M may comprise a reserve pocket 100 of hydrophilic material M in the region of the LAA, wherein upon implantation, the hydrophilic material M swells to enlarge pocket 100 to cover and/or fill the LAA. The hydrophilic material M reserve may comprise a ring or gasket 102 of material M around the circumference of the skirt S so that locating the LAA is achieved no matter the rotational position of the implanted anchoring structure 10. Alternatively, the specific pocket 102 may be provided as described above that is located to the LAA for swelling sealing and/or filling of the LAA. The hydrophilic material M reserve may be formed according to the various embodiments discussed herein, including pocket(s) and/or nanoparticles and/or coating.

Generally, the improved sealing and/or apposition may therefore be improved by including hydrophilic material M at one or more locations on an anchoring structure 10. The hydrophilic material M may be associated or integrated with or incorporated with a skirt S, but this is just one embodiment. Nanoparticles, when employed, may comprise an easily breakable material and/or biodegradable, bioerodable or dissolving material to provide the desired delay in exposing the hydrophilic material M to blood.

With reference now to FIGS. 4A-8, generally, it is to be noted that the embodiments illustrated are substantially symmetrical about a central axis A (as shown in FIG. 4A, for example).

As noted above, the left atrium is not perfectly symmetrical. More specifically, the left atrium comprises an anterior medial tilt. This anterior medial tilt, may lead in some cases to movement of an implanted device attempting to accommodate and/or adapt to the shape of the left atrial chamber. This asymmetry is best shown in FIGS. 1 and 18-20.

The devices shown in the FIGS. 4A-11, and 16-17 comprise a stent frame of a certain shape which is obtained, as the skilled artisan appreciates, by using a mandrel that has the desired shape. The stent frame material is stretched over the mandrel and processed by known means to achieve the desired stent frame shaping.

The stent mandrel of FIG. 18 is essentially a mandrel that results in the shape of, e.g., the symmetrical stent frame of FIG. 4A. The mandrel has substantially equally sized anterior and posterior sections, each of the anterior and posterior sections having substantially the same shape, wherein the "chimney" that forms the valve support of the prosthetic heart valve device is centrally located between the anterior and posterior sections, wherein the resulting valve support is arranged to be over the annulus when implanted. A top structure that may comprise a ring to aid in distributing forces around a greater area may be provided as shown. The mandrel is shown as oversized relative to the atrium which may be desired in order to provide a slightly oversized stent frame that, when expanded, generates strong frictional fit within the heart chamber.

The device of 18B thus comprises a central axis A with the posterior and anterior sections, valve support and top structure are symmetrically disposed in relation to axis A, and wherein the top structure and valve support are effectively aligned along axis A. Top structure may, or may not be present in the various embodiments.

Figure 18B:
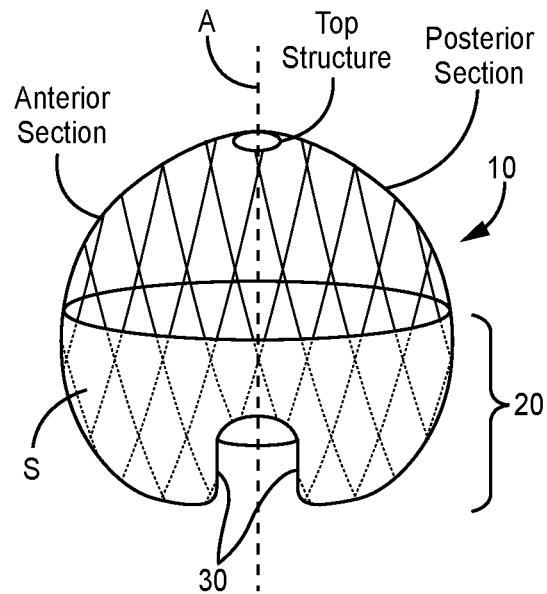
FIG. 18B illustrates a side view of one embodiment of the present invention.
Figure 19B:
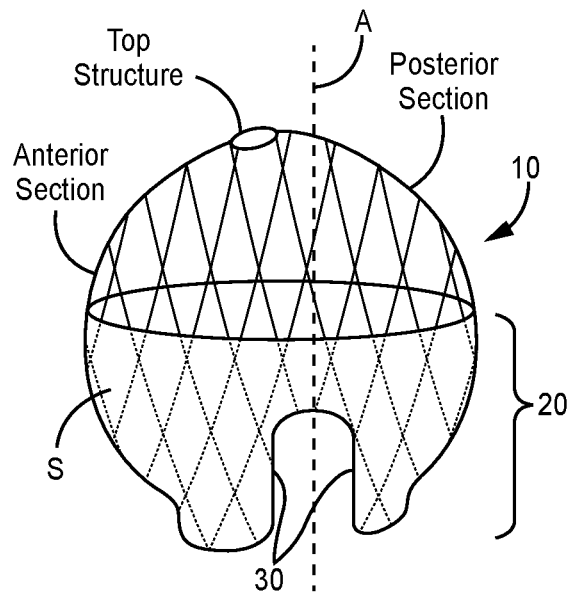
FIG. 19B illustrates a side view of one embodiment of the present invention.

FIG. 19A provides one alternative solution wherein the mandrel comprises an asymmetric "bean" shape and wherein the "chimney" giving rise to the valve support in the resulting stent frame is, as in FIG. 18A, arranged to be over the annulus when the device is implanted. As illustrated in 19A, a posterior portion or section of the mandrel is smaller than the anterior portion or section. Additionally, the anterior portion or section is larger than the anterior portion of FIG. 18A, and the posterior portion or section is smaller than the posterior portion of FIG. 18A. FIG. 19B provides an exemplary device resulting from processing with mandrel of FIG. 19A.

As shown, the arrangement of FIG. 19A allows the anterior section to accommodate or engage more of the left atrium than the arrangement of FIG. 18A while still maintaining the fluid flow path through the valve support, down into the annulus and through the native valve leaflets.

The top structure of FIG. 19B, which may be optional, is now shown as shifted away from axis A and into the anterior section to aid in force transmission and/or distribution.

Figure 20B:
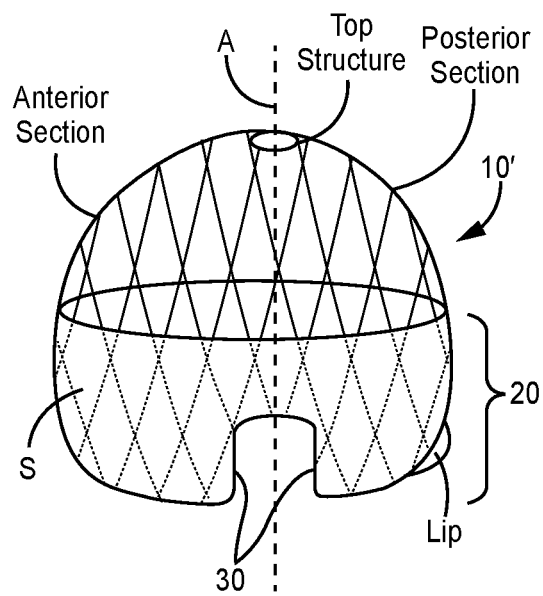
FIG. 20B illustrates a side view of one embodiment of the present invention.

FIG. 20A comprises a mandrel that is the same as in FIG. 18A, with one difference: the posterior base section of the mandrel defines a radially extending lip. The resulting device, shown in FIG. 20B, will thus comprise a radially extending lip which, when expanded, will engage the left atrium on the posterior side of the chamber with more frictional gripping force than the device of FIG. 18B, thus aiding in shifting due to the asymmetry of the atrium after implantation. Top structure is shown as aligned with axis A, as in FIG. 18B.

Figure 21:
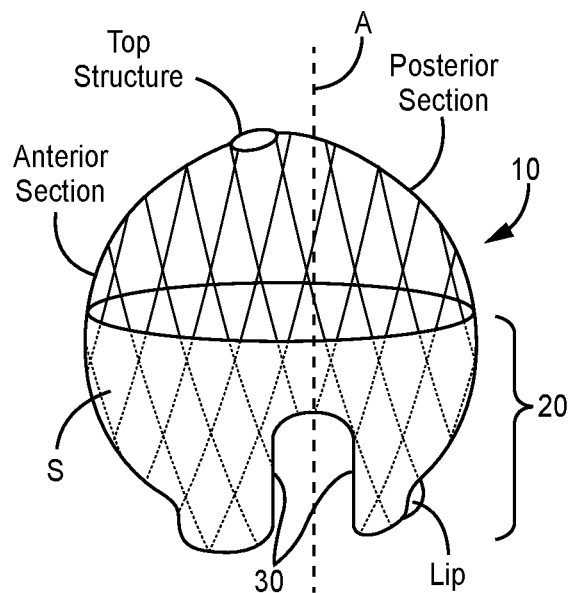
FIG. 21 illustrates a side view of one embodiment of the present invention.

A combination of the device of FIGS. 19B and 20B may be provided as shown in FIG. 21, wherein the frame portion is asymmetrical and the posterior lip structure is provided, and top structure is offset from axis A, with the valve support aligned with axis A and arranged to be positioned over the annulus when implanted. An alternative arrangement may not comprise the top structure, or may comprise the top structure also aligned with axis A.

In all cases, the "chimney" and resulting valve support, are arranged to be perpendicular to the base of the stent. As discussed further above, the length of the "chimney" and resulting valve support may vary and may, or may not, be entirely disposed within the interior of the stent frame.

In any of the described embodiments, the anterior section of the stent frame may comprise a hydrophilic material, e.g., a hydrophilic metal, that expands when exposed to liquid, e.g., blood. The hydrophilic metal may be adapted to expand only radially outwardly to enhance conformance of the anterior section to the chamber, e.g., left atrial, wall on the anterior side. Alternatively, the outer portion of at least a portion of the anterior section may be coated with a hydrophilic material that expands radially outwardly to achieve better conformance with the anterior atrial wall. Still more alternatively, some, or all, of the outer stent frame may comprise a hydrophilic material to enhance expanded conformance (and engagement) with the chamber wall. As described above, the hydrophilic material may be coated with a thin film, and/or encased in nanoparticles, to delay the hydrophilic expansion until the device is released from the delivery catheter into the heart chamber and at least provisionally positioned.

Similarly, the posterior lip of exemplary stent frame in FIG. 20B may be formed and/or defined in the device as a result of the stent frame taking on the mandrel's shape, which includes the lip structure. In this case, the lip is provided on the stent during delivery and implantation. Alternatively, the stent frame in the location of the desired lip may comprise a hydrophilic material, e.g., a hydrophilic metal, or may be coated with a hydrophilic material. The hydrophilic material, whether metal or a coating, may be covered with a thin film. The coating alternative may comprise the hydrophilic material encased in nanoparticles to allow the lip to form only after the device is positioned and implanted. Still more alternatively, the lip may be formed by a hydrophilic pocket as described above.

As shown, the lip is not symmetric around the device and is effectively a raised ridge or lip that extends radially outwardly away from a portion of the base of the prosthetic heart valve device. Alternative lip structures may surround the entire base structure, such that the lip is effectively symmetric.

Moreover, the raised lip may be defined on a portion of the base section that extends downwardly slightly into the annulus when implanted.

Still more alternatively, the raised lip may be defined on, or proximate, a portion of the base section that engages the upper surface of the annulus, a structure that may be referred to as an annular ring.

The raised lip therefore, may increase the oversizing of the base section to improve apposition, fit and prevent shifting movement on implantation.

The asymmetric structures discussed herein require a directional delivery technique to achieve the proper positioning of the device prior to implant. For example, the asymmetric stent frame embodiment of FIG. 19B requires that the posterior section be positioned against the posterior wall of the left atrium. Similarly, the posterior lip section of FIG. 20B will need to be delivered and/or positioned so that the lip is adjacent the posterior wall of the left atrium.

Accordingly, the lip structure may be provided as a consequence of treatment and processing with the mandrel as shown in the Figures. To help in positioning and implanting, the lip may, in some cases, be made smaller than desired, but also adapted to enlarge through hydrophilic expansion as discussed above, in order to tighten the expansion of the device against the posterior wall. In other cases, the lip structure may be entirely formed of a hydrophilic structure as discussed above. In this case, the lip structure only begins to form after the delivery of the prosthetic valve device into the wet chamber which may assist in keeping delivery profiles as low as possible as well as in recapturing and repositioning.

The hydrophilic expansion techniques described herein may be used, either alone or in combination with a mandrel, to create and/or modify the shape of the stent frame and/or lip structure and may be further used to create the lip structure.

The improved prosthetic heart valve devices described herein provide better apposition and fit against the chamber, e.g., left atrium, walls and annulus, thus (1) mitigating shifting of the implanted device as a result of the asymmetry of the heart chamber; (2) improving sealing against relevant tissue which, in turn, assists in preventing PVL The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A device for expanded implantation into the left atrium of a patient's heart, the device comprising:
   an expandable stent frame comprising a posterior section and an anterior section; and
   a base section comprising a posterior section and an anterior section;
   a valve support adapted for supporting at least one prosthetic valve; wherein:
      the posterior section and the anterior section of the expandable stent frame are symmetrically shaped relative to each other;
      a lip extends at least partially around a portion of the base section, the lip extending radially outwardly away from the base section; and
      when the device is implanted and expanded:
         the stent frame is configured to engage the left atrium;
         the base section is configured to engage annular tissue of the left atrium; and
         the lip is configured to engage the annular tissue of the left atrium.

2. The device of claim 1, wherein the lip is disposed on the posterior section of the base section.

3. The device of claim 1, wherein the lip is formed using a mandrel.

4. The device of claim 1, wherein the lip is formed at least in part from a hydrophilic material, wherein the lip is configured to extend radially outwardly away from the base section at least in part from an expansion of the hydrophilic material.

5. The device of claim 1, further comprising a skirt of single layered material operatively attached to a portion of an outer surface of the base section and wherein the skirt comprises hydrophilic material that is integrated into, or coated onto, the single layered material of the skirt to form the lip when wetted.

6. The device of claim 5, wherein the hydrophilic material is coated onto an outer surface of the single layered material of the skirt to form the lip when wetted.

7. The device of claim 6, wherein the hydrophilic material is overcoated with a thin film of material that is biodegradable, dissolvable, bioerodable and/or bioabsorbable when exposed to liquid to enable subsequent exposure of the hydrophilic material to the liquid.

8. The device of claim 6, wherein the hydrophilic material is encased in nanoparticles that are integrated into, or coated onto, the single layered material of the skirt, and wherein the nanoparticles are biodegradable, dissolvable, bioerodable and/or bioabsorbable when exposed to liquid to enable subsequent exposure of the hydrophilic material to the liquid.

9. The device of claim 1, further comprising a skirt of material operatively attached to a portion of an outer surface of at least the posterior section of the base section and wherein at least a portion of the skirt comprises two layers of material, wherein at least one pocket is defined between the two layers of material, and wherein a hydrophilic material is disposed within the at least one pocket of the skirt.

10. The device of claim 9, wherein the hydrophilic material is encased in nanoparticles, and wherein the nanoparticle is breakable, biodegradable, bioerodable and/or bioabsorbable when exposed to liquid to enable subsequent exposure of the hydrophilic material to the liquid.

\* \* \* \* \*

UNITED STATES PATENT AND TRADEMARK OFFICE
CERTIFICATE OF CORRECTION

PATENT NO. : 12,053,375 B2
APPLICATION NO. : 17/163910
DATED : August 6, 2024
INVENTOR(S) : Saravana B. Kumar, Steven D. Kruse and Jeffrey R. Stone Page 1 of 1

It is certified that error appears in the above-identified patent and that said Letters Patent is hereby corrected as shown below:

In the Claims

Column 12 In Claim 1, Line 5 remove "and" after "section;"
Column 12 In Claim 1, Line 7 insert --and-- after "section;"

Signed and Sealed this
Twenty-fifth Day of February, 2025

Coke Morgan Stewart
*Acting Director of the United States Patent and Trademark Office*